(12) United States Patent
Senaldi

(10) Patent No.: US 6,849,260 B2
(45) Date of Patent: Feb. 1, 2005

(54) METHODS AND COMPOSITIONS FOR TREATING IGE-RELATED DISEASE USING NNT-1 INHIBITORS

(75) Inventor: Giorgio Senaldi, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/931,704

(22) Filed: Aug. 16, 2001

(65) Prior Publication Data

US 2002/0041873 A1 Apr. 11, 2002

Related U.S. Application Data

(60) Provisional application No. 60/226,436, filed on Aug. 18, 2000.

(51) Int. Cl.[7] .................. A61K 39/00; C07K 14/52; C07H 21/04
(52) U.S. Cl. ............... 424/185.1; 530/351; 536/23.5
(58) Field of Search ................ 424/185.1, 145.1, 424/136.1; 530/351; 536/23.5, 1; 574/44

(56) References Cited

U.S. PATENT DOCUMENTS

| | | |
|---|---|---|
| 5,741,772 A | 4/1998 | Chang |
| 5,814,649 A | 9/1998 | Amano et al. |
| 6,034,066 A | 3/2000 | Johnson et al. |
| 6,054,294 A | 4/2000 | Chang |
| 6,143,874 A | 11/2000 | Chang |

FOREIGN PATENT DOCUMENTS

| | | |
|---|---|---|
| WO | WO 98/33922 | 8/1998 |
| WO | WO 99/00415 | 1/1999 |
| WO | WO 00/74716 | 12/2000 |

OTHER PUBLICATIONS

Abaza et al, J of Protein Chemistry 11(5): 433–444, 1992.*
Kuby et al, in Immunology, second edition, pp. 85–96, 1994.*
Attwood et al, The babel of bioinformatics, Science 290 (5491): 471–473, Oct. 2000.*
Skolnick et al, From genes to protein structure and function: novel applications of computational approaches in the genomic era, Trends in Biotech. 18(1): 34–39, Jan. 2000.*
Mikayama et al, Molecular cloning and functional expression of a cDNA encoding gycosylation–inhibting factor, Proc. Natl. Acad. Sci, USA vol. 90: 10056–10060, Nov. 1993.*
Arm et al., *Advances in Immunology* "The pathiobiology of Brochial Asthma." 51:323–382 (1992).
Chang, *Nature Biotechnology* "The pharmacological basis of anti–IgE therapy." 18:157–162 (2000).
Rosenwasser, Lanny J., *Journal of Allergy and Clinical Immunology* "New immunopharmacologic approaches to asthma: Role of cytokine antagonism." 105:2 Part 2 S586–S591 (2000).
Senaldi et al., *Proc. Nat'l Acad. Sci.* "Novel neurotrophin–1/B cell–stimulating fac tor–3: A cytokine of the IL–6 family." 96:11458–11463 (1999).
Shi et al., Biochemical and Biophysical Res. Comm. "Computational EST Database Analysis Identifies a Novel Member of the Neuropoietic Cytokine Family." 262:132–138 (1999).
Senaldi et al., "Regulatory Effects of Novel Neurotrophin–1/B Cell–Stimulating Factor–3 (Cardiotrophin–Like Cytokine) on B Cell Function" Journal of Immunology (2002) p. 5690–5698.

* cited by examiner

*Primary Examiner*—Christina Chan
*Assistant Examiner*—Phuong Huynh
(74) *Attorney, Agent, or Firm*—Karen L. Nicastro

(57) ABSTRACT

Disclosed are novel methods and compositions for treating IgE-related diseases using NNT-1 inhibitors. In one embodiment, the present invention relates to a method of treating IgE-related diseases using a selective binding agent to NNT-1. In another embodiment, the present invention relates to a method of treating IgE-related diseases using an NNT-1 expression modulator. Methods of modulating IgE levels, and of diagnosing, preventing and/or treating certain types of allergic diseases using NNT-1 inhibitors are also disclosed.

2 Claims, 10 Drawing Sheets

FIGURE 1

Nucleotide Sequence of Human NNT-1 cDNA

```
  1  ATTAAAGCTT CGCCGGAGCC GCGGCTCGCC CTCCCACTCC GCCAGCCTCC
 51  GGGAGAGGAG CCGCACCCGG CCGGCCCAGC CCCAGCCCCA TGGACCTCCG
101  AGCAGGGGAC TCGTGGGGGA TGTTAGCGTG CCTGTGCACG GTGCTCTGGC
151  ACCTCCCTGC AGTGCCAGCT CTCAATCGCA CAGGGGACCC AGGGCCTGGC
201  CCCTCCATCC AGAAAACCTA TGACCTCACC CGCTACCTGG AGCACCAACT
251  CCGCAGCTTG GCTGGGACCT ATCTGAACTA CCTGGGCCCC CCTTTCAACG
301  AGCCAGACTT CAACCCTCCC CGCCTGGGGG CAGAGACTCT GCCCAGGGCC
351  ACTGTTGACT TGGAGGTGTG GCGAAGCCTC AATGACAAAC TGCGGCTGAC
401  CCAGAACTAC GAGGCCTACA GCCACCTTCT GTGTTACTTG CGTGGCCTCA
451  ACCGTCAGGC TGCCACTGCT GAGCTGCGCC GCAGCCTGGC CCACTTCTGC
501  ACCAGCCTCC AGGGCCTGCT GGGCAGCATT GCGGGCGTCA TGGCAGCTCT
551  GGGCTACCCA CTGCCCCAGC CGCTGCCTGG GACTGAACCC ACTTGGACTC
601  CTGGCCCTGC CCACAGTGAC TTCCTCCAGA AGATGGACGA CTTCTGGCTG
651  CTGAAGGAGC TGCAGACCTG GCTGTGGCGC TCGGCCAAGG ACTTCAACCG
701  GCTCAAGAAG AAGATGCAGC CTCCAGCAGC TGCAGTCACC CTGCACCTGG
751  GGGCTCATGG CTTCTGACTT CTGACCTTCT CCTCTTCGCT CCCCCCC
```

FIGURE 2a

Genomic sequences of the human NNT-1

```
   1 aacctgcgag tgggcctggc ggatgggatt attaaagctt cgccggagcc
  51 gcggctcgcc ctcccactcc gccagcctcc gggagaggag ccgcacccgg
 101 ccggcccagc cccagccccA TGGACCTCCG AGCAGgt--- ----------

-----( >1 kb )----------------------- tgaaaaccca 151 aactagccct gctcttcata acatgacaag cagcgcccca tctgatacct
 201 aaaccgacca agtcacagcc ctccaactca ccctctgcct gcccagacct
 251 caccacatcc ttgstggact caaacctcaa ccgcactaaa tcaaccaaat
 301 cccaagtcta aactaatctg aaacttttaa agtaacccag tccttaaacc
 351 taacctagcc caatgccaat tatatctacc ctagccaaac cctaactgcc
 401 tttgccagtc caaagtgtcc actgatcct caccttggtc ctcactgaaa
 451 atcccagaaa agcatatttc cccactgccc acatccctcc ttacagcacc
 501 caaccctggc ctctggactc ctggtatcct gggatgtcca aactctgcag
 551 tgccatcagc caacaagccc gactcgtcaa atgcacctct ctccttcct
 601 gtccccaccc ttgcaggctg atggaaaggc ctcattgaag tccaactttt
 651 ccccacctaa caccaagaac ggggtgaacc tccacactgc caccgttccc
 701 tgagagtgag cactaaatct ccttcaatct aacccacccc tacacttccc
 751 acactcagga atcacatcct agaatatacc caaaactaag cccataagg
 801 cagcccgacc ctagtggtct aaccctatac cttgcttcct atgggtgagt
 851 ctgttcttgg cggccgcctc tctcctgctt cctcccttag agctgactgt
 901 gctcagcctg ccagctctga catgtgctgt ctcccaccct ctgactcccc
 951 tcaagctgca gtgggactgg aagactggca ggaagctagg gtacaactgg
1001 aacacaggca ggtcgacctg cagtccctag gcctggcccc gtccctccat
1051 gtacacacat atacatgttg gcacacacac agtggcacac atgccaaaga
1101 ctctctcagc tgacacacag atccattctc aagtatctac tgatagacac
1151 tcatgcgtgc caagtcctca tcctcaaaca tacacatgcc tctctttctc
1201 tcccgtcttg ccaggagtgt ttcccctcct ccatccctc tgcctcccat
1251 ctggtgtccc accctcaccc cccacccagc ccaaggtggg gacagacacc
1301 tgaggggctg ccagctgctt ccccgtgtgg gcccggccg cgctcatgct
1351 tctcgtccat cctgcccaca gGGGACTCGT GGGGGATGTT AGCGTGCCTG
1401 TGCACGGTGC TCTGGCACCT CCCTGCAGTG CCAGCTCTCA ATCGCACAGG
```

FIGURE 2b

```
1451 GGACCCAGGG CCTGGCCCCT CCATCCAGAA AACCTATGAC CTCACCCGCT
1501 ACCTGGAGCA CCAACTCCGC AGCTTGGCTG GGACCTATgt gagtatccag
1551 cgtaggaatc tgggagttgg ggaggagtga ggagttgggg aaagacagtc
1601 ctaaccgtgg agggttctgg taaatgatgg ggtgaggagg ggctctttgg
1651 ctcccaccag tcccctgtc tggtctatct cctgcccttc cctcttaggt
1701 ggcccccca cttccccatc cctggcccca ggactaggca tgtgggcagg
1751 cctcgcaccc gccttggccc attgcccac tggctgccag cccagccgcc
1801 cgcctccccc tgggggccgg ggaagtctcc tctgtttaca ccgtgttgtg
1851 gtgtctcttg cgcgggcggg gttgggtggg gacagagggg ccccacctcc
1901 catgcctgcg ttccagctcg cctctgcccc cagacctggg gcctgctgc
1951 tctggaccca ggggcctccc ttccgtctgc ctctcccatc ctagctgggc
2001 ctcctagggg ggtcatgggg gaagggact gtagggaacc caggcagtag
2051 tggcagggg tttagggtgt ggatggaggt tatgctgtaa ggatttgggg
2101 gtggtccaga ggtgttcaga gagcccagga gagaaggaag gagggttgga
2151 ggagccgagg caccatgggg aaccggcccc ctcttcccgt gttcctcttc
2201 cacatcccag accctactct ggagccaggg aaagaaaagg gaagaaggtg
2251 gcggggagc tggctccagc cccaggatac accgaggaaa ttagtttgtc
2301 tctgtgcttg tcagcgtgtg aacctccccc tgggcccttg cctatcccag
2351 gcctctcccc ttgcttctcc cttctttccc agttatacat ctccctcatc
2401 cctttccctg ggccccagcc gctcccccga gggttggaaa gggctctgcc
2451 ctcttcccta taccatgctg tcttccatag ccttcctcct gtcctactca
2501 tgagactgcc tccatttctt ccttctgcaa ccctgctcct atcagctgaa
2551 cccttctttc ggagtgttag tgagtacccg tctctcccca gcccctcagc
2601 tggtgggcct gggtgtgtca gcggcaaatg gggctctggt tccaatgggc
2651 cactctcatc tctctcttgt tccttgtgca gaaaaccttt gcttcactcc
2701 actgccctct ctagttcccg acccttttc tctcctggct ttccctgcca
2751 aatttctcca aggagtggtc tacaccctct gcctccactt cctctccacc
2801 cactcacttc ttaaccccct gcaatctggc ttccaggccc cagcaatggt
2851 tctctccaag gtcgtcaggc acctccttgc caagcccgac agtgttttga
2901 aggctcattc tccttgctgt ctgttttgca gccacactgc tgagcgctgc
2951 tgccttctcg aactcctctt ccttggtctc tgcactctcc tgggccacct
3001 tctacctctc cagctcctcc aggctcctct tcctctctgt cctgccccca
3051 cagcgggcac tctcccaagg tttgcccacc cagccaatca gcacgtcctt
```

FIGURE 2c

```
3101  cctgagcgtc ttgtgcgtct cctcctcctc cttttctac gcctctccat
3151  tggagagctc accaccgcca ctgcttcaac tgtcacctgc atacaaatga
3201  tatccttatt ggaaaaactc agggaggcca tgaacaaaga agcctagcat
3251  ggagacaggg ccagtgtcag gggacacaaa aaatagaaac tttgggagca
3301  ggtatctcct tggtggtgag ccagcggctc tgccctcctc cttccccatc
3351  accctctcct tttcacagCT GAACTACCTG GGCCCCCTT TCAACGAGCC
3401  AGACTTCAAC CCTCCCCGCC TGGGGGCAGA GACTCTGCCC AGGGCCACTG
3451  TTGACTTGGA GGTGTGGCGA AGCCTCAATG ACAAACTGCG GCTGACCCAG
3501  AACTACGAGG CCTACAGCCA CCTTCTGTGT TACTTGCGTG GCCTCAACCG
3551  TCAGGCTGCC ACTGCTGAGC TGCGCCGCAG CCTGGCCCAC TTCTGCACCA
3601  GCCTCCAGGG CCTGCTGGGC AGCATTGCGG GCGTCATGGC AGCTCTGGGC
3651  TACCCACTGC CCCAGCCGCT GCCTGGGACT GAACCCACTT GGACTCCTGG
3701  CCCTGCCCAC AGTGACTTCC TCCAGAAGAT GGACGACTTC TGGCTGCTGA
3751  AGGAGCTGCA GACCTGGCTG TGGCGCTCGG CCAAGGACTT CAACCGGCTC
3801  AAGAAGAAGA TGCAGCCTCC AGCAGCTGCA GTCACCCTGC ACCTGGGGGC
3851  TCATGGCTTC tgacttctga ccttctcctc ttcgctcccc cttcaaaccc
3901  tgctcccact ttgtgagagc cagccctgta tgccaacacc tgttgagcca
3951  ggagacagaa gctgtgagcc tctggcccct tcctggaccg gctgggcgtg
4001  tgatgcgatc agccctgtct cctccccacc tcccaaaggt ctaccgagct
4051  ggggaggagg tacagtaggc cctgtcctgt cctgtttcta caggaagtca
4101  tgctcgaggg agtgtgaagt ggttcaggtt ggtgcagagg cgctcatggc
4151  ctcctgcttc ttgcctacca cttggccagt gcccacccag cccctcaggt
4201  ggcacatctg gagggcaggg gttgaggggc caccaccaca catgcctttc
4251  tggggtgaag ccctttggct gccccactct ccttggatgg gtgttgctcc
4301  cttatcccca aatcactcta tacatccaat tcaggaaaca aacatggtgg
4351  caattctaca caaaaagaga tgagattaac agtgcagggt tggggtctgc
4401  attggaggtg ccctataaac cagaagagaa aatactgaaa gcacagggc
4451  agggacagac cagaccagac ccaggagtct ccaaagcaca gagtggcaaa
4501  caaacccga gctgagcatc aggaccttgc ctcgaattgt cttccagtat
4551  tacggtgcct cttctctgcc cccttcccca gggtatctgt gggttgccag
4601  gctggggagg gcaaccatag ccacaccaca ggatttcctg aaagtttaca
4651  atgcagtagc attttggggt gtagggtggc agctccccaa ggccctgccc
4701  cccagcccca ccactcatg actctaagtg tgttgtatta atatttattt
```

FIGURE 2d

```
4751  atttggagat gttatttatt agatgatatt tattgcagaa tttctattct
4801  tgtattaaca ataaaatgc  ttgccccaga acttagtctc tttgcccagc
4851  ctcacccctc ctggtgctca tcagactctt gccacccctg gctcccactc
4901  cctgcttgcc tctggtggag ctgcacagag ctctgggaag aggccctctt
4951  cctccccgca ctggggcgat gggcgcacct cagacttacc cactgctgct
5001  gccaccacca accccttgat ccctcagtcc tcccacacag cttctgtcca
5051  ccccaggttt ccctcacccc acctttgcta agtcttcctc a
```

FIGURE 3

Amino acid Sequence of Human NNT-1 cDNA

```
      -27                                  1
        MDLR AGDSWGMLAC LCTVLWHLPA VPALNRTGDP GPGPSIQKTY    17

DLTRYLEHQL RSLAGTYLNY LGPPFNEPDF NPPRLGAETL PRATVDLEVW    67

RSLNDKLRLT QNYEAYSHLL CYLRGLNRQA ATAELRRSLA HFCTSLQGLL   117

GSIAGVMAAL GYPLPQPLPG TEPTWTPGPA HSDFLQKMDD FWLLKELQTW   167
                                   198
LWRSAKDFNR LKKKMQPPAA AVTLHLGAHG F*                      198
```

FIGURE 4

Nucleotide Sequence of Murine NNT-1 cDNA

```
  1  TATTATTAAA GCTTCGCCGG AGCCGCGGCT CGCCCTCCCA CTCCGCCAGC
 51  CTCTGGGAGA GGAGCCGCGC CCGGCCGGCC CGGCCCCCAG CCCCATGGAC
101  CTCCGAGCAG GGGACTCGTG GGGGATGTTA GCTTGCCTAT GCACGGTGCT
151  GTGGCACCTC CCTGCAGTGC CAGCTCTTAA TCGCACAGGA GATCCAGGCC
201  CTGGCCCCTC CATCCAGAAA ACCTATGACC TCACCCGCTA CCTGGAGCAT
251  CAACTCCGCA GCTTAGCTGG GACCTACCTG AACTACCTGG GGCCCCCTTT
301  CAACGAGCCT GACTTCAATC CTCCTCGACT GGGGGCAGAA ACTCTGCCCA
351  GGGCCACGGT CAACTTGGAA GTGTGGCGAA GCCTCAATGA CAGGCTGCGG
401  CTGACCCAGA ACTATGAGGC GTACAGTCAC CTCCTGTGTT ACTTGCGTGG
451  CCTCAACCGT CAGGCTGCCA CAGCTGAACT CCGACGTAGC CTGGCCCACT
501  TCTGTACCAG CCTCCAGGGC CTGCTGGGCA GCATTGCAGG TGTCATGGCG
551  ACGCTTGGCT ACCCACTGCC CCAGCCTCTG CCAGGGACTG AGCCAGCCTG
601  GGCCCCTGGC CCTGCCCACA GTGACTTCCT CCAGAAGATG GATGACTTCT
651  GGCTGCTGAA GGAGCTGCAG ACCTGGCTAT GGCGTTCAGC CAAGGACTTC
701  AACCGGCTTA AGAAGAAGAT GCAGCCTCCA GCAGCTTCAG TCACCCTGCA
751  CTTGGAGGCA CATGGTTTCT GACCTCTGAC CCTTAACCCC CACACCTCCA
801  GGCCCAGTCA GCTGTGCTT
```

FIGURE 5

Amino Acid Sequence of Murine NNT-1

```
-27                       1
MDLRAGDSWG MLACLCTVLW HLPAVPALNR TGDPGPGPSI QKTYDLTRYL    23

EHQLRSLAGT YLNYLGPPFN EPDFNPPRLG AETLPRATVN LEVWRSLNDR    73

LRLTQNYEAY SHLLCYLRGL NRQAATAELR RSLAHFCTSL QGLLGSIAGV   123

MATLGYPLPQ PLPGTEPAWA PGPAHSDFLQ KMDDFWLLKE LQTWLWRSAK   173
                      198
DFNRLKKKMQ PPAASVTLHL EAHGF*                            198
```

METHODS AND COMPOSITIONS FOR TREATING IGE-RELATED DISEASE USING NNT-1 INHIBITORS

This application claims the benefit of U.S. Provisional Application No. 60/226,436, filed Aug. 18, 2000, which is hereby incorporated by reference.

BACKGROUND

1. Field of the Invention

The present invention relates generally to novel methods and compositions for treating IgE-related disease using NNT-1 inhibitors. More particularly, the present invention relates to novel methods and compositions for treating IgE-related disease by inhibiting or decreasing the production, activity and/or expression of a neurotrophic factor, recently identified as Novel NeuroTrophic factor 1 ("NNT-1").

2. Description of Related Art

Neurotrophic factors are endogenous, soluble proteins that can stimulate or regulate survival, growth, and/or morphological plasticity of neurons (see Fallon and Laughlin, *Neurotrophic Factors*, Academic Press, San Diego, Calif. [1993]). Because of this physiological role, neurotrophic factors are known to be useful in treating the degeneration of nerve cells and the loss of differentiated function that results from nerve damage.

The known neurotrophic factors belong to several different protein superfamilies of polypeptide growth factors based on their amino acid sequence homology and/or their three-dimensional structure (MacDonald and Hendrikson, *Cell*, 73:421–424 [1993]). One family of neurotrophic factors is the neurotrophin family. This family currently consists of NGF (nerve growth factor), BDNF (brain derived neurotrophic factor), NT-3 (neurotrophin-3), NT-4 (neurotrophin-4), and NT-6 (neurotrophin-6).

CNTF (ciliary neurotrophic factor) and LIF (leukemia inhibitory factor) are cytokine polypeptides that have neurotrophic activity. By virtue of their structural features and receptor components, these polypeptides are related to a family of hematopoietic cytokines that includes IL-6 (interleukin-6), IL-11 (interleukin-11), G-CSF (granulocyte-colony stimulating factor), and oncostatin-M.

Recently, several naturally occurring neurotrophic factors have been identified based on their trophic activity on various neurons. These novel polypeptides, referred to as "novel neurotrophic factors" or "NNT-1," are disclosed in U.S. Pat. No. 5,741,772 (Chang), the disclosure of which is herein incorporated by reference in its entirety. NNT-1, a cytokine of the IL-6 family, was found to be useful in promoting neuron regeneration and restoring neural functions. In addition to novel NNT-1 polypeptides, the Chang patent disclosed, among other things, related biologically active polypeptide fragments and derivatives thereof (i.e. having neurotrophic activity), novel nucleic acid molecules encoding such polypeptides, vectors comprising these nucleic acid molecules, host cells comprising the vectors, antibodies to NNT-1, methods of preparing NNT-1 polypeptides, therapeutic compositions containing NNT-1 polypeptides, assays to screen for inhibitors of NNT-1, transgenic mammals in which the gene(s)encoding the human equivalent of NNT-1 has been disrupted ("knocked out")and methods of treating diseases and disorders of the nervous system using NNT-1.

In addition, the use of NNT-1 to treat certain IgG and IgM-related immunological diseases was identified and discussed in pending PCT WO 98/33922, the disclosure of which is also incorporated herein by reference in its entirety. In that application, evidence was presented that NNT-1 compounds may have a biological activity of modulating the immune system, and in particular, causing an increase in B-cell and T-cell production. Thus, in addition to neurotrophic properties, NNT-1 demonstrates B-cell stimulating activity, which consists of the induction of lymphoid hyperplasia and elevation of serum IgG and IgM. See also Senaldi, et al., *Novel Neurotrophin-1/B Cell-Stimulating Factor-3: A Cytokine Of The IL-6 Family*, Proc. Natl. Acad. Sci.,USA, Vol. 96, pp. 11458–11463 (September 1999).

Of particular interest in the area of immunological disorders are allergy and asthma. Allergy and asthma are debilitating diseases that afflict nearly 20 percent of the population of industrialized countries. For reasons still not well understood, allergic individuals produce increased amounts of IgE with binding specificity for ordinarily innocuous antigens, such as pollen, animal fur, certain foods, etc., collectively termed "allergens." These IgE molecules circulate in the blood and bind to IgE-specific receptors on the surface of basophils and mast cells.

In an allergic reaction, the inhaled or ingested allergens bind to IgE on these mast cells or basophils, crosslink the IgE molecules, and aggregate the underlying receptors, thus triggering the cells to release histamine and the other pharmacological mediators of the symptomatic allergic response. Antigen-specific IgE has thus been shown to play a key role in the physiopathology of allergic disorders. See, Arm, *Advances In Immunology*, 51:323–383 (1992); Rosenwasser, *Journal of Allergy and Clinical Immunology*, 105:S586–S591 (2000); Change, *Nature Biotechnology*, 18:157–162 (2000).

It is well-established that at least one common feature that distinguishes allergic individuals from others is their abnormally high levels of IgE. There is currently no reliable cure for allergy and no approved treatment that corrects the overproduction of IgE. Current drugs for allergic diseases, such as antihistamines, corticosteriods, and bronchodilators ($\beta$-adrenergic receptor antagonists), treat allergic symptoms and concomitant inflammatory reactions. Desensitization immunization with antigens (allergens), which is used mainly in the United States for allergic rhinitis, is not effective for about half of the treated patients. Therefore, a treatment that targets the allergic process, prevents it from occurring, and has fewer side effects than current drugs is desirable.

Accordingly, it is an object of the present invention to provide a method and composition for treating and/or preventing IgE-related diseases such as allergy and asthma. It is a further object of the invention to provide a novel use for NNT-1 inhibitors in the treatment of certain IgE-related immunological diseases and disorders.

It is still a further object of the invention to provide a method of inhibiting antigen-specific IgE production by inhibiting the activity, production and/or expression of NNT-1.

It is still another object of the present invention to provide a method of treating or preventing IgE-related disease using NNT-1 inhibitors.

These and other objects will be apparent to one of ordinary skill in the art from the present disclosure.

SUMMARY OF THE INVENTION

In one embodiment, the present invention relates to a method of treating IgE-related disease comprising administering to a patient a therapeutically effective amount of an NNT-1 inhibitor. In another embodiment, the present invention relates to a method of treating IgE-related disease comprising administering to a patient an NNT-1 inhibitor which is capable of inhibiting binding to at least one polypeptide selected from the group consisting of:
- a) a polypeptide comprising the amino acid sequences of SEQ ID NOS: 2, 4 or 5;
- b) a polypeptide encoded by a nucleic acid sequence of SEQ ID NOS: 1 or 3;
- c) a biologically active fragment of the polypeptides of a) or b); or
- d) a naturally occurring variant of a), b) or c).

In another embodiment, the present invention provides a novel method of modulating IgE levels in a patient comprising administering to said patient a therapeutically effective amount of an NNT-1 inhibitor.

In still another embodiment, the present invention provides a novel method for treating allergic disease comprising administering to a patient a therapeutically effective amount of an NNT-1 inhibitor.

In an additional embodiment, the present invention provides a method of using an NNT-1 inhibitor to modulate the levels of IgE in a patient.

In yet another embodiment, the present invention relates to a method of diagnosing an IgE-related disease or susceptibility to an IgE-related disease comprising:
- a) determining the presence or amount of expression of at least one polypeptide selected from the group consisting of:
  - i) a polypeptide comprising the amino acid sequences of SEQ ID NOS: 2,4, or 5;
  - ii) a polypeptide encoded by a nucleic acid sequence of SEQ ID NOS: 1 or 3;
  - iii) a fragment of the polypeptide of i) or ii) above;
  - iv) a naturally occurring variant of i), ii) or iii); and
- b) diagnosing an IgE-related disease or susceptibility to an IgE-related disease based on the presence or amount of expression of the polypeptide. using NNT-1 inhibitors In still another embodiment, the present invention relates to a method of preventing an IgE-related disease comprising administering to a patient a therapeutically effective amount of an NNT-1 inhibitor.

In still a further embodiment, the present invention relates to a pharmaceutical composition for use in treating IgE-related disease comprising a therapeutically effective amount of an NNT-1 inhibitor.

BRIEF DESCRIPTION OF THE DRAWINGS

FIG. 1 depicts the nucleic acid sequence of the cDNA encoding human NNT-1 (SEQ ID NO:1).

FIGS. 2a–d depicts the nucleic acid sequence of the human genomic DNA for NNT-1 (SEQ ID NO:3).

FIG. 3 depicts the amino acid sequence for human NNT-1 (SEQ ID NO:1) as translated from the cDNA (SEQ ID NO:2). The first 27 amino acids may represent a signal peptide sequence, such that the mature form of NNT-1 starts at the leucine indicated as number 1. The * indicates the stop codon.

FIG. 4 depicts the nucleic acid sequence of the cDNA encoding murine NNT-1 (SEQ ID NO:4).

FIG. 5 depicts the amino acid sequence for murine NNT-1 (SEQ ID NO:5) as translated from the cDNA (SEQ ID NO:4). The first 27 amino acids may represent a signal peptide sequence, such that the mature form of murine NNT-1 starts at the leucine, indicated as number 1. The * indicates the stop codon.

DETAILED DESCRIPTION OF THE INVENTION

Figure 6:
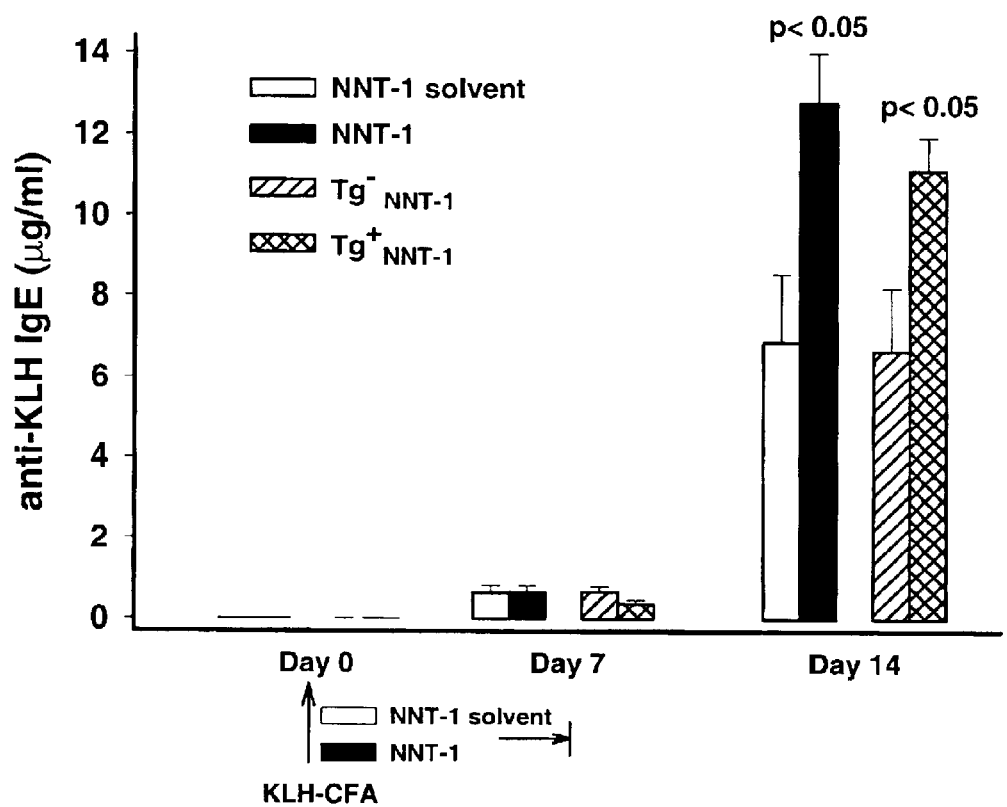
FIG. 6 depicts serum levels of anti-KLH IgE in Balb/c mice treated for seven days with NNT-1 or NNT-1 solvent as a control and in NNT-1 transgenic mice (Tg+) and in littermate controls (Tg−).
Figure 7:
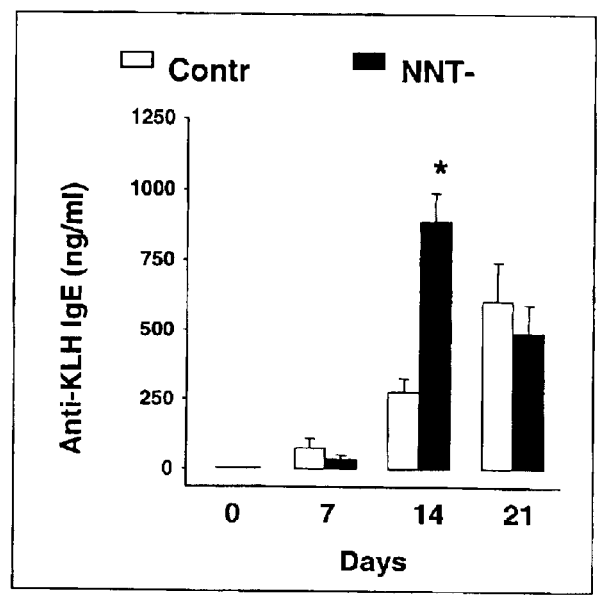
FIG. 7 depict serum levels of anti-KLH IgE in NNT-1 transgenic mice (Tg+) and in littermate controls (Tg−) bled on days 7, 14 and 21.

It has, surprisingly, been found that NNT-1, a novel neurotrophic factor, is also able to induce elevation of total IgE in serum and to stimulate antigen-specific IgE production. The finding that NNT-1 is able to modulate levels of serum IgE strongly suggests that NNT-1 may be involved in the pathogenesis of IgE-related disease, such as allergy and asthma. Pharmacologically attacking or inhibiting NNT-1 may represent a new therapeutic approach to the treatment and/or prevention of certain IgE-related diseases and disorders.

Accordingly, the present invention provides a method for treating IgE-related disease by administering a therapeutically effective amount of an NNT-1 inhibitor, such as an anti-NNT-1 antagonist antibody. Specifically included in the scope of this invention is the use of agents that inhibit or reduce the production, expression or activity of NNT-1, including but not limited to antibodies, peptides, fusion peptides, oligonucleotides, small molecules, soluble receptor proteins, and other agents that function to inhibit or decrease the activity, production or expression of NNT-1, and/or related biologically active polypeptide fragments, derivatives and variants thereof. Also contemplated are agents which similarly effect the NNT-1 receptor (i.e., agents which prevent signal transduction in the NNT-1 receptor) as well as agents that modulate the expression of NNT-1 or its receptor.

The section headings used herein are for organizational purposes only and are not to be construed as limiting the subject matter described. All references cited in this section are expressly incorporated by reference herein.

I. NNT-1 Proteins/Polypeptides, Fragments, Derivatives and Variants Thereof

The term "NNT-1 protein" or "NNT-1 polypeptide" as used herein refers to any protein or polypeptide disclosed or described in, or having the properties described in U.S. Pat. No. 5,471,772. By way of illustration, NNT-1 protein or NNT-1 polypeptide refers to:

(1) an amino acid sequence encoded by NNT-1 nucleic acid molecules as defined in any of the following items:
- (a) the nucleic acid molecule of SEQ ID NO: 1;
- (b) the nucleic acid molecule of SEQ ID NO: 3;
- (c) a nucleic acid molecule encoding the polypeptide of SEQ ID NO: 2, or a biologically active fragment thereof;
- (d) a nucleic acid molecule that encodes a polypeptide that is at least 70 percent identical to the polypeptide of SEQ ID NO: 2;
- (e) a nucleic acid molecule that hybridizes under stringent conditions to any of (a)–(d) above;
- (f) a nucleic acid molecule that is the complement of any of (a)–(e) above; and
- (a') the nucleic acid molecule of SEQ ID NO:4;
- (b') a nucleic acid molecule encoding the polypeptide of SEQ ID NO:5 or a biologically active fragment thereof;

(c') a nucleic acid molecule that encodes a polypeptide that is at least 70 percent identical to the polypeptide of SEQ ID NO:5;

(d') a nucleic acid molecule that hybridizes under stringent conditions to any of (a')–(c') above; and (e') a nucleic acid molecule that is the complement of any of (a')–(d') above;

(2) related biologically active polypeptides and fragments and derivatives thereof;

(3) naturally occurring allelic variants of the NNT-1 gene which result in one or more amino acid substitutions, deletions, and/or insertions as compared to the NNT-1 polypeptide of SEQ ID NO:2 or SEQ ID NO:5, and/or (4) chemically modified derivatives as well as nucleic acid and/or amino acid sequence variants, splice variants, derivatives, and orthologs.

The NNT-1 polypeptides may be naturally occurring full length polypeptides, or truncated polypeptides or peptides (i.e., "fragments"). The polypeptides may be in mature form or they may be attached to a native or heterogeneous signal peptide. For example, human and murine NNT-1 have signal peptides of amino acids −27 to −1 of SEQ ID NOS: 2 and 5, respectively.

The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring NNT-1 polypeptide (i.e., may contain one or more amino acid deletions, insertions, and/or substitutions as compared with naturally occurring NNT-1).

As used herein, the term "fragment" refers to a peptide or polypeptide that is less than the full length amino acid sequence of naturally occurring NNT-1 protein. It may comprise a truncation at the amino terminus (with or without a leader sequence) and/or a truncation at the carboxy terminus of the polypeptide as set forth in SEQ ID NO: 2, allelic variants, orthologs, splice variants and/or variants having one or more amino acid additions or substitutions or internal deletions (where the resulting polypeptide is at least 6 amino acids or more in length) as compared to the amino acid sequence set forth in SEQ ID NO: 2. NNT-1 fragments may result from alternative RNA splicing or from in vivo protease activity and additionally include soluble forms such as those lacking a transmembrane or membrane binding domain. Further, such fragments may be chemically modified and/or may be prepared with or without an amino terminal methionine.

As used herein, the term "biologically active fragment" refers to a fragment that has, qualitatively, a substantially similar type of biological activity as full length, mature NNT-1 polypeptide described above. Preferably, the activity of the fragment is ≧50%, more preferably ≧65%, most preferably ≧80%, of the activity of the full-length polypeptide, as measured by a standard activity assay. Some exemplary fragments include the polypeptides wherein from 1 to 20 amino acids are removed from either the C-terminus, the N-terminus, or both termini, of the NNT-1 polypeptide. Examples of biological activity include the ability to act as a growth factor for neurons (e.g., motor neurons and/or sympathetic neurons) or of modulating the immune system (e.g., causing an increase in B-cell and/or T-cell production).

Fragments and/or derivatives of NNT-1 that are not themselves active in activity assays may be useful as modulators of the NNT-1 receptors in vitro or in vivo, or to prepare antibodies to NNT-1 polypeptides.

As used herein, the term "allelic variants" refers to one of several possible naturally occurring alternate forms of the gene occupying a given locus on a chromosome or a population of organisms.

As used herein, the term "derivative" refers to an NNT-1 polypeptide, protein, fragment, allelic variant, ortholog, splice variant or variant thereof that; 1) has been chemically modified, as for example, by addition of one or more polyethylene glycol molecules, sugars, phosphates, or other such molecules not naturally attached to wild-type NNT-1 polypeptide, and/or 2) contains one or more nucleic acid or amino acid sequence substitutions, deletions, and/or insertions as compared to the NNT-1 amino acid sequence set forth in FIG. 3 (human) or FIG. 5 (murine).

As used herein, the term "ortholog" refers to a polypeptide from another species that corresponds to the NNT-1 polypeptide amino acid sequence as set forth in SEQ ID NO: 2. For example, mouse and human NNT-1 polypeptides are considered orthologs of each other. As used herein, the term "splice variant" refers to a nucleic acid molecule, usually RNA, which is generated by alternative processing of intron sequences in an RNA transcript of an NNT-1 polypeptide amino acid sequence as set forth in SEQ ID NO: 2.

As used herein, the term "variant" refers to an NNT-1 polypeptide comprising amino acid sequences having one or more amino acid substitutions, deletions (such as internal deletions and/or fragments), and/or additions (such as internal additions and/or fusion polypeptides) as compared to the NNT-1 amino acid sequence set forth in SEQ ID NO: 2 (with or without a leader sequence). Variants may be naturally occurring (e.g., NNT-1 polypeptide allelic variants, orthologs and splice variants) or artificially constructed. Such NNT-1 variants may be prepared from the corresponding nucleic acid molecules having a DNA sequence that varies accordingly from the DNA sequence as set forth in SEQ ID NO: 1. For example, NNT-1 variants may have from 1 to 100 (or more than 100) amino acid substitutions, insertions, additions and/or deletions wherein the substitutions may be conservative, non-conservative, or any combination thereof. The amino acid variants of NNT-1 preferably are at least 70% identical to either SEQ ID NO: 2 or SEQ ID NO: 5, more preferably at least about 80% identical, even more preferably at least about 90% identical.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span," which can include the full length of one or both sequences, or a predetermined portion of one or both sequences). Each computer program provides a "default" opening penalty and a "default" gap penalty, and a scoring matrix such as PAM 250. A standard scoring matrix (see Dayhoff et al., in: *Atlas of Protein Sequence and Structure*, vol. 5, supp.3 [1978]) can be used in conjunction with the computer program. The percent identity can then be calculated using an algorithm contained in a program such as FASTA as:

$$\frac{\text{Total number of identical matches}}{[\text{length of the longer sequence} + \text{within the matched span}] [\text{number of gaps introduced into the longer sequence in order to align the two sequences}]} \times 100$$

Polypeptides that are at least 70 percent identical will typically have one or more amino acid substitutions, deletions, and/or insertions as compared with wild type NNT-1. Usually, the substitutions will be conservative so as to have little or no effect on the overall net charge, polarity, or hydrophobicity of the protein but optionally may increase the activity of NNT-1. Conservative substitutions are set forth in Table I below.

TABLE I

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Also contemplated are species homologs or othologs of NNT-1; for example, NNT-1 orthologs from a mammalian species such as dog, cat, mouse, rat, monkey, horse, pig, goat, rabbit, sheep and the like is contemplated in addition to human. The sequences of murine cDNA and protein are provided as SEQ ID NOS: 4 and 5.

As indicated previously, the NNT-1 polypeptide referred to herein also includes chemically modified derivatives, such as glycosylation variants wherein the number and/or type of glycosylation sites has been altered compared to the amino acid sequence set forth in SEQ ID NO: 2. For example, an NNT-1 variant may contain a greater or a lesser number of N-linked glycosylation sites than the amino acid sequence set forth in SEQ ID NO: 2. An N-linked glycosylation site is characterized by the sequence: Asn-X-Ser or Ans-X-Thr, wherein the amino acid residue designated as X may be any amino acid residue other than proline. Alternatively, substitutions which eliminate this sequence will remove an existing N-lined carbohydrate chain. Also contemplated is a rearrangement of N-linked carbohydrate chains wherein one or more N-linked glycosylation sites (typically those naturally occurring) are eliminated and one or more new N-linked sites are created. Additional variants include cysteine variants, wherein one or more cysteine residues are deleted from or substituted for another amino acid (e.g., serine) as compared to the amino acid sequence set forth in SEQ ID NO: 2.

II. Nucleic Acids

As used herein, the term "NNT-1" when used to describe a nucleic acid molecule refers to a nucleic acid molecule or fragment thereof, as set forth above.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, and the like, refers to materials which are found in nature and are not manipulated by man. Similarly, "non-naturally occurring" or "non-native" as used herein refers to a material that is not found in nature or that has been structurally modified or synthesized by man.

The term "stringent conditions" refers to hybridization and washing under conditions that permit only binding of a nucleic acid molecule such as an oligonucleotide or cDNA molecule probe to highly homologous sequences. One stringent wash solution is 0.015 M NaCl, 0.005 M NaCitrate, and 0.1 percent SDS used at a temperature of 55° C.–65° C. Another stringent wash solution is 0.2×SSC and 0.1 percent SDS used at a temperature of between 50° C.–65° C. Where oligonucleotide probes are used to screen cDNA or genomic libraries, the following stringent washing conditions may be used. One protocol uses 6×SSC with 0.05 percent sodium pyrophosphate at a temperature of 35° C.–62° C., depending on the length of the oligonucleotide probe. For example, 14 base pair probes are washed at 35–40° C., 17 base pair probes are washed at 45–50° C., 20 base pair probes are washed at 52–57° C., and 23 base pair probes are washed at 57–63° C. The temperature can be increased 2–3° C. where the background non-specific binding appears high. A second protocol utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45–50° C.

NNT-1 nucleic acid molecules, fragments, and/or derivatives that do not themselves encode polypeptides that are active in activity assays may be useful as hybridization probes in diagnostic assays to test, either qualitatively or quantitatively, for the presence of NNT-1 DNA or RNA in mammalian tissue or bodily fluid samples.

NNT-1 nucleic acid molecules encoding NNT-1 polypeptides attached to native or heterogeneous signal peptides as described herein above are also contemplated.

III. NNT-1 Inhibitors

As used herein, the term "NNT-1 inhibitor" refers to an agent which is capable of inhibiting the production, activity or expression of NNT-1 (as defined above) or its receptor.

Specifically contemplated are agents that bind, antagonize, inhibit or modulate the NNT-1 polypeptide and/or the NNT-1 receptor. Also contemplated are expression modulators which effect either the NNT-1 polypeptide or its receptor, including but not limited to ribozymes and small molecules.

One sub-class of such inhibitors may be referred to as "selective binding agents" or "SBAs." As used herein, "selective binding agent" refers to a molecule which is capable of specifically binding to an NNT-1 polypeptide, fragment, derivative or variant thereof or the NNT-1 receptor. Suitable selective binding agents include, but are not limited to, antibodies and derivatives thereof, polypeptides, fusion polypeptides (i.e., part peptide, part antibody), soluble receptor proteins, small molecules, anti-sense oligonucleotides and other molecules having binding specificity. SBAs may bind to an active or inactive form of the NNT-1 polypeptide, to any portion of the NNT-1 polypeptide and/or to the NNT-1 receptor. Suitable SBAs may be prepared using methods known in the art.

An exemplary NNT-1 polypeptide selective binding agent of the present invention is an antibody, peptide, fusion peptide or soluble NNT-1 receptor protein that is capable of binding a certain portion of the NNT-1 polypeptide (as broadly defined above) and partially or completely inhibiting the binding of NNT-1 to its receptor. Similarly contemplated are selective binding agents, such as an antibody, peptide, fusion peptide, inactive form of NNT-1 or a small molecule that binds or otherwise prevents signal transduction at the site of the NNT-1 receptor.

As used herein, the terms "specific" and "specificity" refer to the ability of the selective binding agents to bind to NNT-1 polypeptides and not to bind to non-NNT-1 polypeptides. It will be appreciated, however, that the selective binding agents may also bind orthologs of the polypeptide as set forth in SEQ ID NO: 2, that is, interspecies versions thereof, such as mouse and rat polypeptides.

A. Antibodies and Derivatives Thereof

A preferred embodiment of the present invention involves the use of selective binding agents such as antibodies and antibody fragments, derivatives and/or variations thereof that bind to either the NNT-1 polypeptide itself or its receptor. The antibodies may be polyclonal including monospecific polyclonal, monoclonal (MAbs), recombinant, chimeric, humanized, complementarity determining regions ("CDR")-grafted, human, single chain, and/or bispecific, hetero-antibodies, as well as fragments, variants or derivatives thereof that are capable of binding NNT-1 and partially or completely neutralizing NNT-1 activity or binding to the NNT-1 receptor, thereby blocking signal transduction.

Antibody fragments include those portions of the antibody which bind to an epitope on the NNT-1 polypeptide, an Fv, Fab, Fab' or F(ab)' fragment, or other fragments, variants, or derivatives thereof. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an NNT-1 polypeptide generally are produced in animals (e.g., rabbits or mice) by means of multiple subcutaneous or intraperitoneal injections of an NNT-1 polypeptide and a suitable adjuvant. It may be useful to conjugate an NNT-1 polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-NNT-1 polypeptide antibody titer.

Monoclonal antibodies directed toward an NNT-1 polypeptide are produced using any method which provides for the production of antibody molecules by continuous cell lines in culture. Examples of suitable methods for preparing monoclonal antibodies include the hybridoma methods of Kohler et al., *Nature*, 256:495–497 (1975) and the human B-cell hybridoma method, Kozbor, *J. Immunol.*, 133:3001 (1984); Brodeur et al., Monoclonal Antibody Production Techniques and Applications, pp. 51–63 (Marcel Dekker, Inc., New York, 1987). Also contemplated are hybridoma cell lines which produce monoclonal antibodies reactive with NNT-1 polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is identical with or homologous to a corresponding sequence in antibodies derived from another species or belonging to another antibody class or subclass. Also included are fragments of such antibodies, so long as they exhibit the desired biological activity. See, U.S. Pat. No. 4,816,567; Morrison et al., *Proc. Natl. Acad. Sci.*, 81:6851–6855 (1985).

Also contemplated is the use of a "humanized" antibody, i.e., prepared so as to prevent or minimize an immune reaction to the antibody when administered to a patient. Methods for humanizing non-human antibodies are well known in the art. See U.S. Pat. Nos. 5,585,089, and 5,693, 762. Generally, a humanized antibody has one or more amino acid residues introduced into it from a source which is non-human. Humanization can be performed, for example, using methods described in the art (Jones et al., *Nature* 321:522–525 (1986); Riechmann et al., *Nature*, 332:323–327 (1988); Verhoeyen et al., *Science* 239:1534–1536 (1988)), by substituting at least a portion of a rodent CDR for the corresponding regions of a human antibody.

Also encompassed by the invention is the use of human antibodies which bind NNT-1 polypeptides. Using transgenic animals (e.g., mice) that are capable of producing a repertoire of human antibodies in the absence of endogenous immunoglobulin production, such antibodies are produced by immunization with an NNT-1 antigen (i.e., one having at least 6 contiguous amino acids), optionally conjugated to a carrier. See, for example, Jakobovits et al., *Proc. Natl. Acad. Sci.*, 90:2551–2555 (1993); Jakobovits et al., *Nature* 362:255–258 (1993); Bruggermann et al., *Year in Immuno.*, 7:33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than e.g., murine) amino acid sequences, including variable regions which are immunospecific for these antigens. See PCT application nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Also contemplated are "fully" human antibodies, wherein not only are the amino acid sequences human, but the glycosylation or other chemical modifications of the antibody are human as well.

Human antibodies may also be produced by the expression of recombinant DNA in host cells or by expression in hybridomas. Such hybridomas are generated by presenting the NNT-1 or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human NNT-1 polypeptide are further disclosed in Chang (U.S. Pat. No. 5,741,772).

In an alternative embodiment, human antibodies can be produced from phage-display libraries (Hoogenboom et al., *J. Mol. Biol.* 227:381 (1991); Marks et al., *J. Mol. Biol.* 222:581 (1991). These processes mimic immune selection through the display of antibody repertoires on the surface of filamentous bacteriophage, and subsequent selection of phage by their binding to an antigen of choice. One such technique is described in PCT Application no. PCT/US98/17364, which describes the isolation of high affinity and functional agonistic antibodies for MPL- and msk-receptors using such an approach.

Chimeric, CDR-grafted, and humanized antibodies are typically produced by recombinant methods. Nucleic acids encoding the antibodies are introduced into host cells and expressed using materials and procedures described herein. In one embodiment, the antibodies are produced in mammalian host cells, such as CHO cells. Monoclonal (e.g., human) antibodies may be produced by the expression of recombinant DNA in host cells or by expression in hybridoma cells as described herein.

The anti-NNT-1 antibodies of the invention may be employed in any known assay method, such as competitive binding assays, direct and indirect sandwich assays, and immunoprecipitation assays (Sola, Monoclonal Antibodies: A Manual of Techniques, pp. 147–158 (CRC Press, Inc., 1987)) for the detection and quantitation of NNT-1 polypeptides. The antibodies will bind NNT-1 polypeptides with an affinity which is appropriate for the assay method being employed.

The selective binding agents, including anti-NNT-1 antibodies, also are useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including antibodies, may be used as therapeutics. In the area of allergy, these therapeutic agents are antagonists in that they reduce or inhibit at least one of the biological activities of an NNT-1 polypeptide. For example, antagonist antibodies of the invention are antibodies (or fragments thereof) which are capable of specifically binding to an NNT-1 polypeptide (or its receptor) or which are capable of inhibiting or eliminating a functional activity of a NNT-1 in vivo or in vitro. In a preferred embodiment, the selective binding agent, e.g., an antagonist antibody, will inhibit the functional activity of an NNT-1 polypeptide by at least about 50%, and preferably by at least about 80%. In another embodiment, the selective binding agent may be an NNT-1 polypeptide antibody that is capable of interacting with an NNT-1 binding partner (a ligand or receptor) thereby inhibiting or eliminating NNT-1 activity in vitro or in vivo. Selective binding agents are identified by screening assays which are well known in the art.

B. Peptides and Derivatives Thereof

Also contemplated by the present invention is the use of peptides, modified peptides and fusion peptides which are capable of specifically binding to NNT-1 polypeptides, fragments, derivatives, variants thereof and/or the NNT-1 receptor.

Specifically contemplated are peptides which may be fused to a homologous polypeptide to form a homodimer or to a heterologous polypeptide to form a heterodimer. Heterologous peptide and polypeptides include, but are not limited to, a polypeptide or peptide which increases stability, such as an immunoglobulin constant region ("the Fc domain") and linkages to polymers such as polyethylene glycol ("PEG") and dextran. When constructed together with a therapeutic protein, an Fc domain can, for example, provide a longer half-life or incorporate such functions as Fc receptor binding. Such modifications are discussed in detail in a patent application entitled, "Modified Peptides as Therapeutic Agents," U.S. Ser. No. 09/428,082, PCT appl. no. WO.99/25044, which is hereby incorporated by reference in its entirety.

IV. Therapeutic Compositions and Administration Thereof

As used herein, the terms "effective amount" and "therapeutically effective amount" refer to the amount of an NNT-1 inhibitor necessary to support one or more biological activities of: 1) inhibiting or reducing the expression, activity or production of the NNT-1; 2) inhibiting or reducing the ability of the NNT-1 polypeptide to bind to its receptor; 3) antagonizing the NNT-1 polypeptide and/or its receptor; 4) decreasing in vivo levels of NNT-1; and/or 5) decreasing serum level of IgE.

Methods of treating various IgE-related diseases or disorders using therapeutic compositions containing NNT-1 inhibitors are within the scope of the present invention. Such compositions may comprise a therapeutically effective amount of an NNT-1 inhibitor in admixture with a pharmaceutically acceptable carrier. The carrier material may be water for injection, preferably supplemented with other materials common in solutions for administration to mammals. Typically, an NNT-1 inhibitor therapeutic compound will be administered in the form of a composition comprising a purified NNT-1 inhibitor in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. An exemplary composition comprises citrate buffer of about pH 4.0–4.5, which may further include NaCl.

The NNT-1 inhibitor compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of NNT-1 inhibitor compositions useful for practicing the present invention may be prepared for storage by mixing the selected composition having the desired degree of purity with optional physiologically acceptable carriers, excipients, or stabilizers (*Remington's Pharmaceutical Sciences*, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The NNT-1 inhibitor composition to be used for in vivo administration must be sterile. This is readily accomplished by filtration through sterile filtration membranes. Where the NNT-1 inhibitor composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intra-arterial, or intralesional routes, or by sustained release systems or implantation device which may optionally involve the use of a catheter. Where desired, the compositions may be administered continuously by infusion, bolus injection or by implantation device. Alternatively or additionally, the NNT-1 inhibitor composition may be administered locally via implantation into the affected area of a membrane, sponge, or other appropriate material on to which the composition has been adsorbed.

Where an implantation device is used, the device may be implanted into any suitable tissue or organ, such as, for example, into a cerebral ventricle or into brain parenchyma, and delivery of an NNT-1 inhibitor composition may be directly through the device via bolus or continuous administration, or via a catheter using continuous infusion.

NNT-1 inhibitor compositions may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamine (Sidman et al, *Biopolymers*, 22: 547–556 [1983]), poly (2-hydroxyethyl-methacrylate) (Langer et al., *J. Biomed. Mater. Res.*, 15: 167–277 [1981] and Langer, *Chem. Tech.*, 12: 98–105 [1982]), ethylene vinyl acetate (Langer et al., supra) or poly-D(−)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA*, 82: 3688–3692 [1985]; Hwang et al., *Proc. Natl. Acad. Sci. USA*, 77: 4030–4034 [1980]; EP 52,322; EP 36,676; EP 88,046; EP 143,949).

In some cases, it may be desirable to use NNT-1 inhibitor compositions in an ex vivo manner, i.e., to treat cells or tissues that have been removed from the patient and are then subsequently implanted back into the patient.

In other cases, NNT-1 inhibitor compositions may be delivered through implanting into patients certain cells that have been genetically engineered to express and secrete an NNT-1 inhibitor. Such cells may be animal or human cells, and may be derived from the patient's own tissue or from another source, either human or non-human. Optionally, the cells may be immortalized. The cells may be implanted into the brain, adrenal gland or into other suitable body tissues or organs of the patient.

In certain situations, it may be desirable to use gene therapy methods for administration of NNT-1 inhibitors to patients suffering from certain immunological disorders. In these situations, anti-sense strands of genomic DNA, cDNA, and/or synthetic DNA encoding the NNT-1 inhibitor or a fragment or variant thereof may be operably linked to a constitutive or inducible promoter that is active in the tissue into which the composition will be injected. This anti-sense NNT-1 inhibitor oligonucleotide, either inserted into a vector, or alone without a vector, can be injected directly. Alternatively, an anti-sense NNT-1 inhibitor DNA construct may be directly injected into muscle tissue where it can be taken up into the cells and expressed in the cells, provided that the anti-sense NNT-1 inhibitor DNA is operably linked to a promoter that is active in muscle tissue such as cytomegalovirus (CMV) promoter, Rous sarcoma virus (RSV) promoter, or muscle creatine kinase promoter. Typically, the DNA construct may include (in addition to the anti-sense NNT-1 inhibitor DNA and a promoter), vector sequence obtained from vectors such as adenovirus vector, adeno-associated virus vector, a retroviral vector, and/or a herpes virus vector. The vector/DNA construct may be admixed with a pharmaceutically acceptable carrier(s) for injection.

An effective amount of the NNT-1 inhibitor composition (s) to be employed therapeutically will depend, for example, upon the therapeutic objectives such as the indication for which the NNT-1 inhibitor is being used, the route of administration, and the condition of the patient. Accordingly, it will be necessary for the therapist to titer the dosage and modify the route of administration as required to obtain the optimal therapeutic effect. Typically, a clinician will administer the NNT-1 inhibitor composition until a dosage is reached that achieves the desired effect. The NNT-1 inhibitor composition may therefore be administered as a single dose, or as two or more doses (which may or may not contain the same amount of NNT-1 inhibitor) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

V. Conditions to be Treated with NNT-1 Inhibitor Compositions

Since NNT-1 is expressed in immune system cells and in hematopoietic cells, NNT-1 inhibitors may be useful to treat diseases caused by immune disorders and/or diseases caused by disorders of the hematopoietic system. Specifically, NNT-1 inhibitors may be used to treat patients who suffer from IgE-related immune diseases and disorders. There are several primary IgE-related immune disorders that are potential targets for NNT-1 inhibitors. Examples of such diseases include, but are not limited to, Type I allergic diseases, allergic rhinitis, eczema, dermatitis, pollinosis, dermatitis, anaphylactic shock, and asthma. Other diseases or disorders influenced by the dysfunction of allergic responses are encompassed within the scope of the invention.

The finding that NNT-1 stimulates antigen-specific IgE production importantly suggests that NNT-1 is specifically involved in the pathogenesis of allergy. By inhibiting or significantly decreasing the activity, expression or production of NNT-1 using NNT-1 inhibitors, the level of serum IgE may be reduced. A reduction in serum IgE levels has been shown to reduce symptoms of IgE related disease.

A non-exclusive list of additional acute and chronic IgE-related diseases which may be treated, diagnosed, ameliorated, or prevented by using NNT-1 inhibitors include:

Diseases involving abnormal cell proliferation, including, but not limited to, cancer, arteriosclerosis and vascular restenosis. Other diseases influenced by the inappropriate proliferation of cells are also encompassed within the scope of the invention.

Diseases and conditions relating to dysfunction of the immune system, including, but not limited to, rheumatoid arthritis, psioriatic arthritis, inflammatory arthritis, osteoarthritis, inflammatory joint disease, autoimmune disease, multiple sclerosis, lupus, diabetes, inflammatory bowel disease, transplant rejection, and graft vs. host disease. Other diseases influenced by the dysfunction of the immune system are encompassed within the scope of the invention.

Reproductive diseases and disorders, including, but not limited to, infertility, miscarriage, preterm labor and delivery, and endometriosis. Other diseases of the reproductive system are encompassed within the scope of the invention.

Other diseases caused by or related by undesirable levels of IgE are encompassed within the scope of the invention.

VI. Diagnostic and Other Related Uses of NNT-1 Inhibitors

In addition to use as therapeutics, the NNT-1 inhibitor compositions disclosed herein may have additional IgE-related uses. For example, these compositions may further be used for in vivo and in vitro diagnostic purposes, such as in labeled form to detect the presence of NNT-1 and/or IgE in a body fluid.

NNT-1 inhibitors, particularly antibodies, may also be employed in any known assay method, such as competitive binding assays, direct and indirect sandwich assays, and immunoprecipitation assays (Sola, Monoclonal Antibodies: A Manual of Techniques, pp. 147–158 (CRC Press, Inc., 1987)) for the detection and quantitation of NNT-1 polypeptides as an indicator of serum IgE levels. The antibodies will bind NNT-1 polypeptides with an affinity which is appropriate for the assay method being employed.

For diagnostic applications, in certain embodiments, NNT-1 inhibitors may be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase, or horseradish peroxidase (Bayer et al., *Meth. Enz.*, 184:138–163 (1990)).

Competitive binding assays rely on the ability of a labeled standard (e.g., an NNT-1 polypeptide, or an immunologically reactive portion thereof) to compete with the test sample analyte (an NNT-1 polypeptide) for binding with a limited amount of anti NNT-1 antibody. The amount of an NNT-1 polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The assays described below provide examples of methods useful for identifying compounds that could inhibit NNT-1 activity. For ease of reading, the following definition is used herein for describing the assays: "Test molecule(s)" refers to the molecule(s) that is under evaluation as an inhibitor of NNT-1, typically by virtue of its potential ability to block the interaction of NNT-1 with its receptor.

The NNT-1 receptor may be isolated, for example, by expression cloning using labeled (e.g., iodinated) NNT-1.

Several types of in vitro assays using purified protein may be conducted to identify those compounds that disrupt NNT-1 activity. Such disruption may be accomplished by a compound that typically inhibits the interaction of NNT-1 with its receptor.

In one assay, purified NNT-1 protein or a fragment thereof (prepared for example using methods described above) can be immobilized by attachment to the bottom of the wells of a microtiter plate. Radiolabeled NNT-1 receptor, as well as the test molecule(s) can then be added either one at a time or simultaneously to the wells. After incubation, the wells can be washed and counted using a scintillation counter for radioactivity to determine the degree of NNT-1/receptor binding in the presence of the test molecule. Typically, the molecule will be tested over a range of concentrations, and a series of control "wells" lacking one or more elements of the test assays can be used for accuracy in evaluating the results. A variation of this assay involves attaching the receptor to the wells, and adding radiolabeled NNT-1 along with the test molecule to the wells. After incubation and washing, the wells can be counted for radioactivity.

Several means including radiolabeling are available to "mark" NNT-1. For example, NNT-1 protein can be radiolabeled using 125-I or 35-S. Alternatively, a fusion protein of NNT-1 wherein the DNA encoding NNT-1 is fused to the coding sequence of a peptide such as the c-myc epitope. NNT-1-myc fusion protein can readily be detected with commercially available antibodies directed against myc.

An alternative to microtiter plate type of binding assays comprises immobilizing either NNT-1 or its receptor on agarose beads, acrylic beads or other types of such inert substrates. The inert substrate containing the NNT-1 or its receptor can be placed in a solution containing the test molecule along with the complementary component (either receptor or NNT-1 protein) which has been radiolabeled or fluorescently labeled; after incubation, the inert substrate can be precipitated by centrifugation, and the amount of binding between NNT-1 and receptor can be assessed using the methods described above. Alternatively, the insert substrate complex can be immobilized in a column and the test molecule and complementary component passed over the column. Formation of the NNT-1/receptor complex can then be assessed using any of the techniques set forth above, i.e., radiolabeling, antibody binding, or the like.

Another type of in vitro assay that is useful for identifying a molecule to inhibit NNT-1 activity is the Biacore assay system (Pharmacia, Piscataway, N.J.) using a surface plasmon resonance detector system and following the manufacturer's protocol. This assay essentially involves covalent binding of either NNT-1 or its receptor to a dextran-coated sensor chip which is located in a detector. The test molecule and the complementary component can then be injected into the chamber containing the sensor chip either simultaneously or sequentially, and the amount of binding of NNT-1/receptor can be assessed based on the change in molecular mass which is physically associated with the dextran-coated side of the of the sensor chip; the change in molecular mass can be measured by the detector system.

In some cases, it may be desirable to evaluate two or more test molecules together for use in decreasing or inhibiting NNT-1 activity. In these cases, the assays set forth above can be readily modified by adding such additional test molecule (s) either simultaneously with, or subsequently to, the first test molecule. The remainder of steps in the assay can be as set forth above.

The NNT-1 inhibitors disclosed herein, including anti-NNT-1 antibodies, also are useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

VII. Use of Transgenic Mammals

Also included within the scope of the present invention are methods of modulating IgE levels using non-human mammals such as mice, rats, rabbits, goats, or sheep in which the gene (or genes) encoding the human equivalent of NNT-1 has been disrupted ("knocked out") such that the level of expression of this gene is significantly decreased or completely abolished. Such mammals may be prepared using techniques and methods such as those described in U.S. Pat. No. 5,557,032. The methods of the present invention further include modulating IgE levels using non-human mammals such as mice, rats, rabbits, goats, or sheep in which the gene (or genes) encoding the NNT-1 (either the native form of NNT-1 for the mammal or a heterologous NNT-1 gene) is over expressed by the mammal, thereby creating a "transgenic" mammal. Such transgenic mammals may be prepared using well known methods such as those described in U.S. Pat. No. 5,489,743 and PCT patent application no. WO94/28122, published 8 Dec. 1994.

These non-human animals may be used for drug candidate screening. In such screening, the impact of a drug candidate on the animal may be measured. For example, drug candidates may decrease or increase the expression of the NNT-1 gene. In certain embodiments, the amount of NNT polypeptide that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to prevent or inhibit a pathological condition. In other examples, the overproduction of a particular metabolic product such as a fragment of a polypeptide may result in, or be associated with, a disease or pathological condition. In such cases, one may test a drug candidate's ability to decrease the production of such a metabolic product or its ability to prevent or inhibit a pathological condition.

The following examples are intended for illustration purposes only, and should not be construed as limiting the scope of the invention in any way.

EXAMPLES

Standard methods for library preparation, DNA cloning, and protein expression are set forth in Sambrook et al. (*Molecular Cloning: A Laboratory Manual*, Cold Spring Harbor Laboratory Press, Cold Spring Harbor, N.Y. [1989]) and in Ausubel et al, eds. (*Current Protocols in Molecular Biology*, Wiley, New York, N.Y. [1995]).

Example I

Induction of Anti-keyhole Limpet Hemocyanin (KLH) and Total IgE.

To induce anti-KLH (i.e., antigen-specific) IgE, mice (Balb/c females of 9–11 wk and 19–21 g, Charles River Laboratories, Wilmington, Mass.) were immunized on day 0 by the subcutaneous injection of 100 ug of KLH (Pierce, Rockford, Ill.) in complete Freund's adjuvant (CFA). Starting on day 0, mice received 7 consecutive daily i.p. injections of 5 mg/Kg of NNT-1 or NNT-1 solvent alone as a control and were then bled on days 4, 7, and 14. This above experiment was repeated using 3 mg/Kg of NNT-1 and bleeding mice before KLH immunization and 7 and 14 days after.

Detectable levels of serum anti-KLH IgE were observed in 2/8 NNT-1-treated mice and in 0/10 controls 7 days after KLH immunization and in 6/8 NNT-1-treated mice and in 2/10 controls 14 days after KLH immunization. Anti-KLH IgE were not detectable in any of the mice 4 days after KLH immunization. When the experiment was repeated, NNT-1-treated mice showed higher levels of anti-KLH IgE than control mice 14 days after KLH immunization (FIG. 6). Anti-KLH IgE antibodies were not detectable in any of the mice before KLH immunization and were detectable in only a few of the mice 7 days after KLH immunization.

Example II

NNT-1 transgenic (Tg+) mice and control littermates (Tg–) were immunized as above (5 mg/Kg) and bled before immunization and 7 and 14 days after. NNT-1 Tg+ mice overexpress NNT-1 encoding sequence engineered in a gene containing the liver-specific apoE promoter. To induce total IgE, mice (Balb/c as above) received one daily i.p. injection of 5 mg/Kg of NNT-1 for 7 consecutive days. Control mice received NNT-1 solvent alone. Mice were then bled the day following the day of last injection.

NNT-1 Tg+ mice showed higher levels of anti-KLH IgE antibodies than control littermates 14 days after KLH immunization (FIG. 6). Anti-KLH IgE antibodies were not detectable in any of the Tg+ or Tg– mice before KLH immunization and were detectable in only a few of them 7 days after KLH immunization. In an experiment of total IgE induction, NNT-1-treated mice showed a 22% increase of serum total IgE compared to control mice.

Example III

Detection of Anti-KLH IgE and of Total IgE.

Anti-KLH IgE antibodies were measured in serum by ELISA. Briefly, plates were coated with KLH in PBS, blocked, and added with dilutions of standard and test samples. Captured anti-KLH IgE were revealed using an anti-mouse IgE biotinylated antibody and neutravidin-conjugated horse radish peroxidase. Total IgE were also measured in serum by ELISA. In this assay, plates were coated with an anti-mouse IgE antibody in PBS, blocked, and added with dilutions of standard and test samples. Captured IgE were revealed as above. Results were expressed in ug/ml and analyzed with the Student t test.

While the present invention has been described in terms of preferred embodiments, it was understood that variations and modifications will occur to those skilled in the art. Therefore, it was intended that the appended claims cover all such equivalent variations which would come within the scope of the invention as claimed.

What is claimed is:

1. A method for increasing antigen-specific IgE production comprising administering to a patient a therapeutically effective amount of a polypeptide comprising SEQ ID NO 2 or SEQ ID NO 5.

2. A method for increasing antigen-specific IgE production comprising administering to a patient a therapeutically effective amount of a polypeptide encoded by a nucleic acid sequence comprising SEQ ID NO 1, 3 or 4.

* * * * *

SEQUENCE LISTING

<160> NUMBER OF SEQ ID NOS: 5

<210> SEQ ID NO 1
<211> LENGTH: 797
<212> TYPE: DNA
<213> ORGANISM: Homo sapiens
<220> FEATURE:
<221> NAME/KEY: CDS
<222> LOCATION: (90)..(764)
<223> OTHER INFORMATION:
<221> NAME/KEY: mat_peptide
<222> LOCATION: (171)..()
<223> OTHER INFORMATION: Met at -27

<400> SEQUENCE: 1

```
attaaagctt cgccggagcc gcggctcgcc ctcccactcc gccagcctcc gggagaggag      60
ccgcacccgg ccggcccagc cccagccccc atg gac ctc cga gca ggg gac tcg     113
                                 Met Asp Leu Arg Ala Gly Asp Ser
                                     -25                      -20 tgg ggg atg tta gcg tgc ctg tgc acg gtg ctc tgg cac ctc cct gca     161
Trp Gly Met Leu Ala Cys Leu Cys Thr Val Leu Trp His Leu Pro Ala
            -15                 -10                      -5 gtg cca gct ctc aat cgc aca ggg gac cca ggg cct ggc ccc tcc atc     209
Val Pro Ala Leu Asn Arg Thr Gly Asp Pro Gly Pro Gly Pro Ser Ile
        -1  1                5                       10 cag aaa acc tat gac ctc acc cgc tac ctg gag cac caa ctc cgc agc     257
Gln Lys Thr Tyr Asp Leu Thr Arg Tyr Leu Glu His Gln Leu Arg Ser
     15                  20                      25 ttg gct ggg acc tat ctg aac tac ctg ggc ccc cct ttc aac gag cca     305
Leu Ala Gly Thr Tyr Leu Asn Tyr Leu Gly Pro Pro Phe Asn Glu Pro
 30                  35                      40                  45 gac ttc aac cct ccc cgc ctg ggg gca gag act ctg ccc agg gcc act     353
Asp Phe Asn Pro Pro Arg Leu Gly Ala Glu Thr Leu Pro Arg Ala Thr
                 50                      55                  60 gtt gac ttg gag gtg tgg cga agc ctc aat gac aaa ctg cgg ctg acc     401
Val Asp Leu Glu Val Trp Arg Ser Leu Asn Asp Lys Leu Arg Leu Thr
             65                      70                  75 cag aac tac gag gcc tac agc cac ctt ctg tgt tac ttg cgt ggc ctc     449
Gln Asn Tyr Glu Ala Tyr Ser His Leu Leu Cys Tyr Leu Arg Gly Leu
         80                      85                  90 aac cgt cag gct gcc act gct gag ctg cgc cgc agc ctg gcc cac ttc     497
Asn Arg Gln Ala Ala Thr Ala Glu Leu Arg Arg Ser Leu Ala His Phe
     95                     100                     105 tgc acc agc ctc cag ggc ctg ctg ggc agc att gcg ggc gtc atg gca     545
Cys Thr Ser Leu Gln Gly Leu Leu Gly Ser Ile Ala Gly Val Met Ala
110                     115                     120                 125 gct ctg ggc tac cca ctg ccc cag ccg ctg cct ggg act gaa ccc act     593
Ala Leu Gly Tyr Pro Leu Pro Gln Pro Leu Pro Gly Thr Glu Pro Thr
                    130                     135                 140
```

```
tgg act cct ggc cct gcc cac agt gac ttc ctc cag aag atg gac gac      641
Trp Thr Pro Gly Pro Ala His Ser Asp Phe Leu Gln Lys Met Asp Asp
        145                 150                 155 ttc tgg ctg ctg aag gag ctg cag acc tgg ctg tgg cgc tcg gcc aag      689
Phe Trp Leu Leu Lys Glu Leu Gln Thr Trp Leu Trp Arg Ser Ala Lys
    160                 165                 170 gac ttc aac cgg ctc aag aag aag atg cag cct cca gca gct gca gtc      737
Asp Phe Asn Arg Leu Lys Lys Lys Met Gln Pro Pro Ala Ala Ala Val
175                 180                 185 acc ctg cac ctg ggg gct cat ggc ttc tgacttctga ccttctcctc            784
Thr Leu His Leu Gly Ala His Gly Phe
190             195 ttcgctcccc ccc                                                       797
```

<210> SEQ ID NO 2
<211> LENGTH: 225
<212> TYPE: PRT
<213> ORGANISM: Homo sapiens

<400> SEQUENCE: 2

```
Met Asp Leu Arg Ala Gly Asp Ser Trp Gly Met Leu Ala Cys Leu Cys
    -25                 -20                 -15

Thr Val Leu Trp His Leu Pro Ala Val Pro Ala Leu Asn Arg Thr Gly
    -10                 -5          -1  1                   5

Asp Pro Gly Pro Gly Pro Ser Ile Gln Lys Thr Tyr Asp Leu Thr Arg
                10                  15                  20

Tyr Leu Glu His Gln Leu Arg Ser Leu Ala Gly Thr Tyr Leu Asn Tyr
            25                  30                  35

Leu Gly Pro Pro Phe Asn Glu Pro Asp Phe Asn Pro Pro Arg Leu Gly
        40                  45                  50

Ala Glu Thr Leu Pro Arg Ala Thr Val Asp Leu Glu Val Trp Arg Ser
    55                  60                  65

Leu Asn Asp Lys Leu Arg Leu Thr Gln Asn Tyr Glu Ala Tyr Ser His
70                  75                  80                  85

Leu Leu Cys Tyr Leu Arg Gly Leu Asn Arg Gln Ala Ala Thr Ala Glu
                90                  95                  100

Leu Arg Arg Ser Leu Ala His Phe Cys Thr Ser Leu Gln Gly Leu Leu
            105                 110                 115

Gly Ser Ile Ala Gly Val Met Ala Ala Leu Gly Tyr Pro Leu Pro Gln
        120                 125                 130

Pro Leu Pro Gly Thr Glu Pro Thr Trp Thr Pro Gly Pro Ala His Ser
    135                 140                 145

Asp Phe Leu Gln Lys Met Asp Asp Phe Trp Leu Leu Lys Glu Leu Gln
150                 155                 160                 165

Thr Trp Leu Trp Arg Ser Ala Lys Asp Phe Asn Arg Leu Lys Lys Lys
                170                 175                 180

Met Gln Pro Pro Ala Ala Ala Val Thr Leu His Leu Gly Ala His Gly
            185                 190                 195

Phe
```

<210> SEQ ID NO 3
<211> LENGTH: 5087
<212> TYPE: DNA
<213> ORGANISM: Homo sapiens
<220> FEATURE:
<221> NAME/KEY: misc_feature
<222> LOCATION: (137)..(138)
<223> OTHER INFORMATION: product = "INTERVENING UNSEQUENCED REGION

OF >1KB"

<400> SEQUENCE: 3

```
aacctgcgag tgggcctggc ggatgggatt attaaagctt cgccggagcc gcggctcgcc        60
ctcccactcc gccagcctcc gggagaggag ccgcacccgg ccggcccagc cccagcccca       120
tggacctccg agcaggttga aacccaaac tagccctgct cttcataaca tgacaagcag        180
cgccccatct gatacctaaa ccgaccaagt cacagccctc caactcaccc tctgcctgcc       240
cagacctcac cacatccttg tggactcaaa cctcaaccgc actaaatcaa ccaaatccca       300
agtctaaact aatctgaaac ttttaaagta acccagtcct taaacctaac ctagcccaat       360
gccaattata tctaccctag ccaaaccta actgcctttg ccagtccaaa gtgtccactg         420
aatcctcacc ttggtcctca ctgaaaatcc cagaaaagca tatttcccca ctgcccacat       480
ccctccttac agcacccaac cctggcctct ggactcctgg tatcctggga tgtccaaact      540
ctgcagtgcc atcagccaac aagcccgact cgtcaaatgc acctctctcc cttcctgtcc       600
ccacccttgc aggctgatgg aaaggcctca ttgaagtcca acttttcccc acctaacacc      660
aagaacgggg tgaacctcca cactgccacc gttccctgag agtgagcact aaatctcctt       720
caatctaacc ccaccctaca cttcccacac tcaggaatca catcctagaa tatacccaaa      780
actaagcccc ataaggcagc ccgacccctag tggtctaacc ctataccttg cttcctatgg     840
gtgagtctgt tcttggcggc cgcctctctc ctgcttcctc ccttagagct gactgtgctc      900
agcctgccag ctctgacatg tgctgtctcc caccctctga ctcccctcaa gctgcagtgg      960
gactggaaga ctggcaggaa gctagggtac aactggaaca caggcaggtc gacctgcagt     1020
ccctaggcct ggccccgtcc ctccatgtac acacatatac atgttggcac acacacagtg     1080
gcacacatgc caaagactct ctcagctgac acacagatcc attctcaagt atctactgat      1140
agacactcat gcgtgccaag tcctcatcct caaacataca catgcctctc tttctctccc      1200
gtcttgccag gagtgtttcc cctcctccat cccctctgcc tcccatctgg tgtcccaccc      1260
tcacccccca cccagcccaa ggtggggaca gacacctgag gggctgccag ctgcttcccc      1320
gtgtgggccc gggccgcgct catgcttctc gtccatcctg cccacagggg actcgtgggg      1380
gatgttagcg tgcctgtgca cggtgctctg gcacctccct gcagtgccag ctctcaatcg      1440
cacagggac ccagggcctg gccccctccat ccagaaaacc tatgacctca cccgctacct      1500
ggagcaccaa ctccgcagct tggctgggac ctatgtgagt atccagcgta ggaatctggg      1560
agttggggag gagtgaggag ttggggaaag acagtcctaa ccgtggaggg ttctggtaaa     1620
tgatggggtg aggagggct ctttggctcc caccagtccc cctgtctggt ctatctcctg       1680
cccttccctc ttaggtggcc ccccacttc cccatccctg gccccaggac taggcatgtg       1740
ggcaggcctc gcacccgcct tggcccattg ccccactggc tgccagccca gccgcccgcc     1800
tcccctggg ggccggggaa gtctcctctg tttacaccgt gttgtggtgt ctcttgcgcg        1860
ggcggggttg ggtggggaca gaggggcccc acctcccatg cctgcgttcc agctcgcctc     1920
tgcccccaga cctggggccc tgctgctctg gaccagggg cctcccttcc gtctgcctct       1980
cccatcctag ctgggcctcc tagggggtc atggggaag gggactgtag gaacccagg         2040
cagtagtggc aggggttta gggtgtggat ggaggttatg ctgtaaggat ttgggggtgg       2100
tccagaggtg ttcagagagc ccaggagaga aggaaggag gttggaggag ccgaggcacc       2160
atggggaacc ggcccctct tcccgtgttc ctcttccaca tcccagaccc tactctggag       2220
ccagggaaag aaaagggaag aaggtggcgg gggagctggc tccagcccca ggatacaccg     2280
```

-continued

```
aggaaattag tttgtctctg tgcttgtcag cgtgtgaacc tcccccctggg cccttgccta  2340 tcccaggcct ctccccttgc ttctcccttc tttcccagtt atacatctcc ctcatccctt  2400
tccctgggcc ccagccgctc ccccgagggt tggaaagggc tctgccctct tccctatacc  2460
atgctgtctt ccatagcctt cctcctgtcc tactcatgag actgcctcca tttcttcctt  2520
ctgcaaccct gctcctatca gctgaaccct tctttcggag tgttagtgag tacccgtctc  2580
tccccagccc ctcagctggt gggcctgggt gtgtcagcgg caaatggggc tctggttcca  2640
atgggccact ctcatctctc tcttgttcct tgtgcagaaa acctttgctt cactccactg  2700
ccctctctag ttcccgaccc ttttctctc ctggctttcc ctgccaaatt tctccaagga  2760
gtggtctaca ccctctgcct ccacttcctc tccacccact cacttcttaa cccctgcaa  2820 tctggcttcc aggcccagc aatggttctc tccaaggtcg tcaggcacct ccttgccaag  2880
cccgacagtg ttttgaaggc tcattctcct tgctgtctgt tttgcagcca cactgctgag  2940
cgctgctgcc ttctcgaact cctcttcctt ggtctctgca ctctcctggg ccaccttcta  3000
cctctccagc tcctccaggc tcctcttcct tctctgtcctg cccccacagc gggcactctc  3060
ccaaggtttg cccacccagc caatcagcac gtccttcctg agcgtcttgt gcgtctcctc  3120
ctcctccttt ttctacgcct ctccattgga gagctcacca ccgccactgc ttcaactgtc  3180
acctgcatac aaatgatatc cttattggaa aaactcaggg aggccatgaa caaagaagcc  3240
tagcatggag acagggccag tgtcagggga cacaaaaat agaaactttg ggagcaggta  3300
tctccttggt ggtgagccag cggctctgcc ctcctccttc cccatcaccc tctccttttc  3360
acagctgaac tacctgggcc cccctttcaa cgagccagac ttcaaccctc cccgcctggg  3420
ggcagagact ctgcccaggg ccactgttga cttggaggtg tggcgaagcc tcaatgacaa  3480
actgcggctg acccagaact acgaggccta cagccacctt ctgtgttact tgcgtggcct  3540
caaccgtcag gctgccactg ctgagctgcg ccgcagcctg gcccacttct gcaccagcct  3600
ccagggcctg ctgggcagca ttgcgggcgt catggcagct ctgggctacc cactgcccca  3660
gccgctgcct gggactgaac ccacttggac tcctggccct gcccacagtg acttcctcca  3720
gaagatggac gacttctggc tgctgaagga gctgcagacc tggctgtggc gctcggccaa  3780
ggacttcaac cggctcaaga agaagatgca gcctccagca gctgcagtca ccctgcacct  3840
gggggctcat ggcttctgac ttctgacctt ctcctcttcg ctcccccttc aaaccctgct  3900
cccactttgt gagagccagc cctgtatgcc aacacctgtt gagccaggag acagaagctg  3960
tgagcctctg gcccttcct ggaccggctg ggcgtgtgat gcgatcagcc ctgtctcctc  4020
cccacctccc aaaggtctac cgagctgggg aggaggtaca gtaggccctg tcctgtcctg  4080
tttctacagg aagtcatgct cgagggagtg tgaagtggtt caggttggtg cagaggcgct  4140
catggcctcc tgcttcttgc ctaccacttg gccagtgccc acccagcccc tcaggtggca  4200
catctggagg gcaggggttg aggggccacc accacacatg cctttctggg gtgaagccct  4260
ttggctgccc cactctcctt ggatgggtgt tgctcccctta tccccaaatc actctataca  4320
tccaattcag gaaacaaaca tggtggcaat tctacacaaa aagagatgag attaacagtg  4380
cagggttggg gtctgcattg gaggtgccct ataaaccaga agagaaaata ctgaaagcac  4440
aggggcaggg acagaccaga ccagacccag gagtctccaa agcacagagt ggcaaacaaa  4500
acccgagctg agcatcagga ccttgcctcg aattgtcttc cagtattacg gtgcctcttc  4560
tctgccccct ttcccagggt atctgtgggt tgccaggctg gggagggcaa ccatagccac  4620
```

-continued

```
accacaggat tcctgaaag tttacaatgc agtagcattt tggggtgtag ggtggcagct    4680
ccccaaggcc ctgcccccca gccccaccca ctcatgactc taagtgtgtt gtattaatat    4740
ttatttattt ggagatgtta tttattagat gatatttatt gcagaatttc tattcttgta    4800
ttaacaaata aaatgcttgc cccagaactt agtctctttg cccagcctca cccctcctgg    4860
tgctcatcag actcttgcca ccctggctc ccactccctg cttgcctctg gtggagctgc    4920
acagagctct gggaagaggc cctcttcctc cccgcactgg ggcgatgggc gcacctcaga    4980 cttaccccact gctgctgcca ccaccaaccc cttgatccct cagtcctccc acacagcttc    5040
tgtccacccc aggtttccct caccccacct tgctaagtc ttcctca                  5087
```

<210> SEQ ID NO 4
<211> LENGTH: 819
<212> TYPE: DNA
<213> ORGANISM: Murine
<220> FEATURE:
<221> NAME/KEY: CDS
<222> LOCATION: (95)..(769)
<223> OTHER INFORMATION:
<221> NAME/KEY: mat_peptide
<222> LOCATION: (176)..()
<223> OTHER INFORMATION:
<221> NAME/KEY: mat_peptid
<222> LOCATION: (176)..(769)
<223> OTHER INFORMATION:
<221> NAME/KEY: sig_peptide
<222> LOCATION: (95)..(175)
<223> OTHER INFORMATION:

<400> SEQUENCE: 4

```
tattattaaa gcttcgccgg agccgcggct cgccctccca ctccgccagc ctctgggaga      60
ggagccgcgc ccggccggcc cggcccccag cccc atg gac ctc cga gca ggg gac    115
                                       Met Asp Leu Arg Ala Gly Asp
                                                     -25 tcg tgg ggg atg tta gct tgc cta tgc acg gtg ctg tgg cac ctc cct      163
Ser Trp Gly Met Leu Ala Cys Leu Cys Thr Val Leu Trp His Leu Pro
 -20              -15                 -10                  -5 gca gtg cca gct ctt aat cgc aca gga gat cca ggc cct ggc ccc tcc      211
Ala Val Pro Ala Leu Asn Arg Thr Gly Asp Pro Gly Pro Gly Pro Ser
         -1  1                   5                  10 atc cag aaa acc tat gac ctc acc cgc tac ctg gag cat caa ctc cgc      259
Ile Gln Lys Thr Tyr Asp Leu Thr Arg Tyr Leu Glu His Gln Leu Arg
             15                  20                  25 agc tta gct ggg acc tac ctg aac tac ctg ggg ccc cct ttc aac gag      307
Ser Leu Ala Gly Thr Tyr Leu Asn Tyr Leu Gly Pro Pro Phe Asn Glu
 30                  35                  40 cct gac ttc aat cct cct cga ctg ggg gca gaa act ctg ccc agg gcc      355
Pro Asp Phe Asn Pro Pro Arg Leu Gly Ala Glu Thr Leu Pro Arg Ala
45                  50                  55                  60 acg gtc aac ttg gaa gtg tgg cga agc ctc aat gac agg ctg cgg ctg      403
Thr Val Asn Leu Glu Val Trp Arg Ser Leu Asn Asp Arg Leu Arg Leu
                 65                  70                  75 acc cag aac tat gag gcg tac agt cac ctc ctg tgt tac ttg cgt ggc      451
Thr Gln Asn Tyr Glu Ala Tyr Ser His Leu Leu Cys Tyr Leu Arg Gly
             80                  85                  90 ctc aac cgt cag gct gcc aca gct gaa ctc cga cgt agc ctg gcc cac      499
Leu Asn Arg Gln Ala Ala Thr Ala Glu Leu Arg Arg Ser Leu Ala His
         95                 100                 105 ttc tgt acc agc ctc cag ggc ctg ctg ggc agc att gca ggt gtc atg      547
Phe Cys Thr Ser Leu Gln Gly Leu Leu Gly Ser Ile Ala Gly Val Met
    110                 115                 120
```

-continued

```
gcg acg ctt ggc tac cca ctg ccc cag cct ctg cca ggg act gag cca    595
Ala Thr Leu Gly Tyr Pro Leu Pro Gln Pro Leu Pro Gly Thr Glu Pro
125                 130                 135                 140 gcc tgg gcc cct ggc cct gcc cac agt gac ttc ctc cag aag atg gat    643
Ala Trp Ala Pro Gly Pro Ala His Ser Asp Phe Leu Gln Lys Met Asp
                145                 150                 155 gac ttc tgg ctg ctg aag gag ctg cag acc tgg cta tgg cgt tca gcc    691
Asp Phe Trp Leu Leu Lys Glu Leu Gln Thr Trp Leu Trp Arg Ser Ala
        160                 165                 170 aag gac ttc aac cgg ctt aag aag aag atg cag cct cca gca gct tca    739
Lys Asp Phe Asn Arg Leu Lys Lys Lys Met Gln Pro Pro Ala Ala Ser
            175                 180                 185 gtc acc ctg cac ttg gag gca cat ggt ttc tgacctctga cccttaaccc      789
Val Thr Leu His Leu Glu Ala His Gly Phe
        190                 195 ccacacctcc aggcccagtc agctgtgctt                                    819

<210> SEQ ID NO 5
<211> LENGTH: 225
<212> TYPE: PRT
<213> ORGANISM: Murine

<400> SEQUENCE: 5

Met Asp Leu Arg Ala Gly Asp Ser Trp Gly Met Leu Ala Cys Leu Cys
        -25                 -20                 -15

Thr Val Leu Trp His Leu Pro Ala Val Pro Ala Leu Asn Arg Thr Gly
    -10                  -5                  -1  1               5

Asp Pro Gly Pro Gly Pro Ser Ile Gln Lys Thr Tyr Asp Leu Thr Arg
                10                  15                  20

Tyr Leu Glu His Gln Leu Arg Ser Leu Ala Gly Thr Tyr Leu Asn Tyr
            25                  30                  35

Leu Gly Pro Pro Phe Asn Glu Pro Asp Phe Asn Pro Pro Arg Leu Gly
        40                  45                  50

Ala Glu Thr Leu Pro Arg Ala Thr Val Asn Leu Glu Val Trp Arg Ser
    55                  60                  65

Leu Asn Asp Arg Leu Arg Leu Thr Gln Asn Tyr Glu Ala Tyr Ser His
70                  75                  80                  85

Leu Leu Cys Tyr Leu Arg Gly Leu Asn Arg Gln Ala Ala Thr Ala Glu
                90                  95                  100

Leu Arg Arg Ser Leu Ala His Phe Cys Thr Ser Leu Gln Gly Leu Leu
            105                 110                 115

Gly Ser Ile Ala Gly Val Met Ala Thr Leu Gly Tyr Pro Leu Pro Gln
        120                 125                 130

Pro Leu Pro Gly Thr Glu Pro Ala Trp Ala Pro Gly Pro Ala His Ser
    135                 140                 145

Asp Phe Leu Gln Lys Met Asp Phe Trp Leu Leu Lys Glu Leu Gln
150                 155                 160                 165

Thr Trp Leu Trp Arg Ser Ala Lys Asp Phe Asn Arg Leu Lys Lys Lys
                170                 175                 180

Met Gln Pro Pro Ala Ala Ser Val Thr Leu His Leu Glu Ala His Gly
            185                 190                 195

Phe
```